United States Patent [19]
Wachter et al.

[11] Patent Number: 5,770,185
[45] Date of Patent: Jun. 23, 1998

[54] DEODORIZING PREPARATIONS

[75] Inventors: Rolf Wachter, Duesseldorf; Karl-Heinz Maurer, Erkrath; Holger Tesmann, Juechen, all of Germany

[73] Assignee: Henkel Kommanditgesellschaft auf Aktien, Duesseldorf, Germany

[21] Appl. No.: 663,130

[22] PCT Filed: Dec. 8, 1994

[86] PCT No.: PCT/EP94/04084

§ 371 Date: Jun. 17, 1996

§ 102(e) Date: Jun. 17, 1996

[87] PCT Pub. No.: WO95/16429

PCT Pub. Date: Jun. 22, 1995

[30] Foreign Application Priority Data

Dec. 17, 1993 [DE] Germany ............... 43 43 264.6

[51] Int. Cl.⁶ ............... A61K 7/32; A61K 7/00; A61K 31/19; A61K 31/20

[52] U.S. Cl. ............... 424/65; 424/400; 424/401; 514/557; 514/558

[58] Field of Search ............... 424/65, 400, 401, 424/66, 67, 68

[56] References Cited

U.S. PATENT DOCUMENTS 4,005,189  1/1977  Reese et al. ............... 424/47

FOREIGN PATENT DOCUMENTS

| | | |
|---|---|---|
| 006234 | 1/1980 | European Pat. Off. . |
| 347664 | 12/1989 | European Pat. Off. . |
| 1 437 366 | 3/1963 | France . |
| 1468454 | 1/1962 | Germany . |
| 2721297 | 11/1978 | Germany . |

*Primary Examiner*—Shelley A. Dodson
*Attorney, Agent, or Firm*—Ernest G. Szoke; Wayne C. Jaeschke; Real J. Grandmaison

[57] ABSTRACT

The process of suppressing body odor by applying to the skin a topical composition containing fat-soluble hydroxycarboxylic acid esters obtained by esterification of polybasic, optionally acetylated hydroxycarboxylic acids containing 3 to 6 carbon atoms by reaction with fatty acids containing 12 to 30 carbon atoms, fatty acid esters of $C_{12-22}$ fatty acids and $C_{1-4}$ alcohols or with hydroxyl compounds selected from the group consisting of (a) fatty alcohols containing 12 to 30 carbon atoms,
(b) fatty acid esters of $C_{12-22}$ fatty acids and polyols containing 2 to 6 carbon atoms and 2 to 6 hydroxyl groups,
(c) epoxyalkanes containing 12 to 30 carbon atoms,
(d) alkyl glycosides corresponding to the formula $R^1O(C_6H_{10}O)_x$—H, in which $R^1$ is an alkyl group containing 8 to 16 carbon atoms and x representing the average degree of oligomerization of the glycoside unit $(C_6H_{10}O)$, has a value of 1 to 4, and
(e) adducts of 1 to 8 moles of ethylene oxide with the hydroxyl compounds (a) to (d).

4 Claims, No Drawings

DEODORIZING PREPARATIONS

BACKGROUND OF THE INVENTION

This invention relates to the use of fat-soluble hydroxycarboxylic acid esters as deodorizing agents in topical preparations for suppressing body odor.

The troublesome odor which accompanies perspiration in human beings is caused mainly by bacterial decomposition of the initially odorless perspiration on the skin and in clothing. Accordingly, either perspiration-inhibiting preparations or antimicrobial formulations have hitherto been used to suppress body odor. Odor-masking perfumes and odor-absorbing substances, for example polymers, have also been proposed, but show only limited effectiveness. Both the perspiration-inhibiting astringent substances and the antimicrobial agents bring with them the danger of irritation and incompatibility when regularly applied to the skin.

Accordingly, there is a constant need to find dermatologically safe, highly compatible deodorizing agents which do not affect the natural skin flora, even in the event of long-term application.

DISCUSSION OF RELATED ART

Certain esters of hydroxycarboxylic acids, for example the ethyl lactate or the triethyl citrate, are known as non-microbicidal deodorizing agents from Cosmetics & Toiletries, Vol. 95, July 1980, pages 48 to 50. The effect of these esters was attributed to esterase inhibition under the effect of the acid released from bacteria of the skin flora during the enzymatic hydrolysis by esterases.

DESCRIPTION OF THE INVENTION

It has now been found that fat-soluble partial esters of polybasic hydroxycarboxylic acids have a considerably greater esterase-inhibiting effect than the short-chain hydroxycarboxylic acid esters mentioned in pH-stabilized aqueous media (buffered to pH 6). In addition, the fat-soluble partial esters of polybasic hydroxy compounds—by virtue of their ready compatibility with the skin—are particularly suitable for use as deodorizing agents in topical preparations.

The present invention relates to the use of fat-soluble hydroxycarboxylic acid esters obtainable by esterification of polybasic, optionally acetylated hydroxycarboxylic acids containing 3 to 6 carbon atoms by reaction with fatty acids containing 12 to 30 carbon atoms, fatty acid esters of $C_{12-22}$ fatty acids and $C_{1-4}$ alcohols or with hydroxyl compounds from the group consisting of (a) fatty alcohols containing 12 to 30 carbon atoms,
(b) fatty acid esters of $C_{12-22}$ fatty acids and polyols containing 2 to 6 C atoms and 2 to 6 hydroxyl groups,
(c) epoxyalkanes containing 12 to 30 carbon atoms,
(d) alkyl glycosides corresponding to the formula $R^1O(C_6H_{10}O)_x$—H, in which $R^1$ is an alkyl group containing 8 to 16 carbon atoms and x, the average degree of oligomerization of the glycoside unit $(C_6H_{10}O)$, has a value of 1 to 4 and
(e) adducts of 1 to 8 moles of ethylene oxide with the hydroxyl compounds (a) to (d)

as deodorizing agents in topical preparations. In one preferred embodiment, the partial esters of the hydroxycarboxylic acids with hydroxyl compounds (b) to (e) or salts thereof are used as the fat-soluble esters.

Partial esters in the context of the present invention are esters in which at least one of the carboxyl groups of the polybasic hydroxycarboxylic acid is still unesterified.

Suitable polybasic hydroxycarboxylic acids are, for example, malic acid, mucic acid, tartronic acid, tartaric acid and pyruvic acid (DL tartaric acid) or mesotartaric acid and citric acid. The fat-soluble partial esters of citric acid and tartaric acid or acetyl citric acid or monoacetyl or diacetyl tartaric acid are preferred. The use of the acetylated hydroxycarboxylic acids is particularly preferred in the case of tartaric acid in order largely to prevent the self-condensation of the hydroxycarboxylic acids.

The lipophilic partial esters are obtained in known manner by reaction with fatty acids or alcohols containing 12 to 30 carbon atoms. In the reaction with fatty acids, the hydroxyl group of the hydroxycarboxylic acids is esterified. By reaction with hydroxyl compounds, preferably one of the carboxyl groups of the hydroxycarboxylic acids is esterified. Suitable fatty acids are, for example, lauric acid, palmitic acid, stearic acid, oleic acid and erucic acid or technical mixtures of such fatty acids, for example coconut oil fatty acid cuts containing 12 to 18 carbon atoms or palm kernel oil fatty acid, tallow fatty acid or palmitic/stearic acid mixtures. Suitable alcohols are, for example, cetostearyl alcohol, cocofatty alcohol cuts containing 12 to 18 or 12 to 14 carbon atoms, hydrogenated tallow alcohol, behenyl alcohol, triacontanol, sterols such as, for example cholesterol or phytosterol and tocopherols.

Reaction of the polybasic hydroxycarboxylic acids with fatty acids and simple esters involves transesterification reactions in which the hydroxyl group of the hydroxycarboxylic acids is esterified. Reaction with fatty acid polyesters containing free hydroxyl groups results for the most part in partial esterification of the carboxyl function of the hydroxycarboxylic acids and, to a very limited extent, in transesterification with the hydroxyl group of the hydroxycarboxylic acids.

Preferred fatty acid polyol esters are, for example, glycerol monostearate, hydrogenated tallow fatty acid monoglyceride, sorbitan monooleate, sorbitan sesqistearate, propylene glycol monopalmitate, pentaerythritol dimyristate, diethylene glycol monostearate. The esterification products of optionally acetylated citric acid or tartaric acid and fatty acid monoglycerides containing 12 to 18 carbon atoms are preferably used as fat-soluble partial esters.

The preparation of the fat-soluble partial esters is known from the literature and is described, for example, in DE 14 68 454. The suitability of such esters as antioxidants is known from that document. The high compatibility of such fat-soluble hydroxycarboxylic acid partial esters with the skin is also known from FR 1 437 366. A few suitable products are commercially available as emulsifiers and auxiliaries for the food industry. They include, for example, Lamegin ZE 309®: a citric acid ester of the monoglyceride of hydrogenated tallow fatty acid (acid value around 70, saponification value around 305)

Lamegin DW 8000®: an ester of diacetyl tartaric acid with the monoglyceride of hydrogenated tallow fatty acid (acid value around 100, saponification value around 510).

The fat-soluble hydroxycarboxylic acid partial esters suitable for use in accordance with the invention are preferably used as sole deodorizing component in the deodorizing cosmetic preparations. Accordingly, the present invention also relates to deodorizing cosmetic preparations containing around 0.5 to 10% by weight of lipophilic hydroxycarboxylic acid partial esters obtainable by reaction of polybasic, optionally acetylated hydroxycarboxylic acids containing 2 to 4 carbon atoms with fatty acids or alcohols containing 12 to 30 carbon atoms or with fatty acid esters of $C_{12-22}$ fatty acids and alcohols containing 1 to 4 carbon atoms or polyols containing 2 to 6 carbon atoms and 2 to 6 hydroxyl groups in an aqueous, emulsion-like, aqueous/alcoholic or water-free carrier. The esters of citric acid or tartaric acid are preferably present as fat-soluble hydroxycarboxylic acid partial esters. The esters of citric acid and tartaric acid with tocopherols in a molar ratio of 1:1 to 1:2 also show particularly high esterase-inhibiting activity. Suitable tocopherols are natural tocopherols ($\alpha$-tocopherol, $\beta$-tocopherol or $\gamma$-tocopherol) and mixtures of these substances and synthetic analogs.

In order to utilize the particular advantages of these non-antimicrobial deodorants, the preparations according to the invention should preferably be free from antimicrobial agents. On the other hand, an addition of antibacterial or anti-perspiratory components can further enhance their deodorizing effect.

The aqueous, emulsion-like, aqueous/alcoholic or water-free preparations suitable as carriers may be liquid, paste-like or solid. They may be liquid lotions or low-viscosity emulsions which are applied to the skin from pump atomizers or by means of aerosol propellent gases. They may also be thickened lotions or emulsions which may be applied from roll-on dispensers. Finally, the preparations according to the invention may also be formulated as deodorizing emollients or creams, as deodorizing stick preparations or deodorizing soaps.

The fat-soluble hydroxycarboxylic acid partial esters are incorporated in the usual way by solubilization with lower alcohols, such as ethanol or isopropanol, and typical solubilizers or by emulsification using known emulsifiers. Preferred emulsifiers for incorporating the hydroxycarboxylic acid partial esters suitable for use in accordance with the invention in aqueous and aqueous/alcoholic preparations are the adducts of ethylene oxide (EO) with linear fatty alcohols, with fatty acids, with fatty acid partial glycerides or fatty acid sorbitan esters. Other lipophilic co-emulsifiers, preferably cetostearyl alcohol or glycerol monostearate, are preferably used for stable emulsification. In addition, the deodorizing preparations according to the invention may contain any auxiliaries and additives required for the particular form of application, for example cosmetic oils, fats, waxes, glycerol, propylene glycol, water-soluble polymers, organophilic clays and dyes and fragrances, complexing agents, anti-oxidants, antiperspirants (for example Al hydroxychloride) and preservatives. Cosmetic agents, for example for firming, moisturizing or refatting the skin, may also be added.

The following Examples are intended to illustrate the invention:

EXAMPLES

1. Determination of the esterase-inhibiting effect of the partial esters according to the invention The esterase activity was determined in a test system containing pig's liver esterase in an aqueous solution of p-nitrophenyl butyrate buffered to pH 6. The esterase activity was reflected in cleavage of the p-nitrophenyl butyrate with release of the p-nitrophenol of which the extinction coefficient was measured for 3 minutes in a photometer at 410 nm (25° C.) and enabled the molar substrate conversion to be calculated as a measure of the enzyme activity.

The esterase-inhibiting effect of the test substances was determined as residual esterase activity after a contact time of 15 minutes of the test substances on the esterase solution similarly to the methods described above. In the following Tables, it is expressed in % of the uninhibited esterase activity.

TABLE I

| | Residual esterase activity using | |
|---|---|---|
| Test substance | 1000 ppm | 5000 ppm |
| Ester of citric acid and hydrogenated tallow fatty acid monoglyceride (Lamegin ZE 309) | 0 | 0 |
| Ester of diacetyl tartaric acid and hydrogenated tallow fatty acid monoglyceride (Lamegin DW 8000) | 10 | 0 |
| Citric acid tocopherol ester (1:2) | 1 | 0 |
| Triethyl citrate (comparison) | 84% | 62% |

TABLE II

| | Residual esterase activity using | | |
|---|---|---|---|
| Test substance | 100 ppm | 500 ppm | 5000 ppm |
| Esterification product of 1 mole of tartaric acid and 1 mole of lauryl alcohol | 17 | 0 | 0 |
| Esterification product of 1 mole of citric acid and 2 moles of the adduct of 7 moles of ethylene oxidel with 1 mote of lauryl/myristyl (2:1) alcohol | — | 90 | 32 |
| Citric acid tri-2-hydroxy-alkyl ($C_{12-18}$) ester (of citric acid with 1,2-epoxy-$C_{12-18}$-alkane) | — | 46 | 7 |
| Mucic acid dialkyl ($C_{8/10}$) ester | — | 80 | 23 |

2. Application Examples

1. Roll-on deodorants

| | a | b | c | d |
|---|---|---|---|---|
| Glycerol (mono/di) stearate/palmitate (around 50% monoglyceride, around 50% stearate) | 4 | 5 | 5 | 5 |
| Cetostearyl alcohol + 12 EO | 1.5 | 1 | 1 | 1 |
| Cetostearyl alcohol + 20 EO | 1.5 | 2 | 2 | 2 |
| Cetyl palmitate | — | 1 | 1 | 1 |
| Cetostearyl alcohol | — | 1.5 | 1.5 | 1.5 |
| 2-Octyl dodecanol | 3.5 | 2 | 2 | 2 |
| Di-n-octyl ether | — | 2 | 2 | 2 |
| $\alpha$-Tocopherol citric acid ester (2:1) | 2.5 | 3 | — | — |
| Hydrogenated tallow fatty acid mono-glyceride citric acid ester (Lamegin ® ZE 309) | — | — | 3 | — |
| Hydrogenated tallow fatty acid mono-glyceride diacetyl tartaric acid ester (Lamegin ® DW 8000) | — | — | — | 3 |
| Glycerol | 5 | 3 | 3 | 3 |
| Carbopol ® 980, 2% in $H_2O$ (Na polyacrylate gel) | 15 | — | — | — |
| Ethanol (98.8%) | 10 | — | — | — |
| Water, NaOH to pH 6 | 57 | 79.5 | 79.5 | 79.5 |

What is claimed is:

1. The process of suppressing body odor comprising applying to the skin a topical composition containing fat-soluble hydroxycarboxylic acid esters obtained by esterification of polybasic, optionally acetylated hydroxycarboxylic acids containing 3 to 6 carbon atoms by reaction with fatty acids containing 12 to 30 carbon atoms, fatty acid esters of $C_{12-22}$ fatty acids and $C_{1-4}$ alcohols or with hydroxyl compounds selected from the group consisting of (a) fatty alcohols containing 12 to 30 carbon atoms, (b) fatty acid esters of $C_{12-22}$ fatty acids and polyols containing 2 to 6 carbon atoms and 2 to 6 hydroxyl groups, (c) epoxyalkanes containing 12 to 30 carbon atoms, (d) alkyl glycosides corresponding to the formula $R^1O(C_6H_{10}O)_x$—H, in which $R^1$ is an alkyl group containing 8 to 16 carbon atoms and x representing the average degree of oligomerization of the glycoside unit $(C_6H_{10}O)$, has a value of 1 to 4, and (e) adducts of 1 to 8 moles of ethylene oxide with the hydroxyl compounds (a) to (d).

2. A process as in claim 1 wherein said topical composition contains the partial esters of said hydroxycarboxylic acids with said hydroxyl compounds (a) to (e) or salts thereof.

3. A process as in claim 2 wherein said partial esters comprise the esterification products of optionally acylated citric acid or tartaric acid and fatty acid monoglycerides containing 12 to 18 carbon atoms.

4. A process as in claim 1 wherein said fat-soluble hydroxycarboxylic acid esters are present in said topical composition in an amount of from about 0.5% to 10% by weight, based on the weight of said topical composition.

* * * * *